United States Patent
Ida (10) Patent No.: US 8,711,657 B2
(45) Date of Patent: Apr. 29, 2014

(54) CONVERTER AND MEASURING APPARATUS

(71) Applicant: Advantest Corporation, Tokyo (JP)

(72) Inventor: Taiichiro Ida, Gunma (JP)

(73) Assignee: Advantest Corporation, Tokyo (JP)

( * ) Notice: Subject to any disclaimer, the term of this patent is extended or adjusted under 35 U.S.C. 154(b) by 0 days.

(21) Appl. No.: 13/749,703

(22) Filed: Jan. 25, 2013

(65) Prior Publication Data

US 2013/0182530 A1 Jul. 18, 2013

Related U.S. Application Data (63) Continuation of application No. PCT/JP2011/005167, filed on Sep. 14, 2011.

(30) Foreign Application Priority Data

Sep. 30, 2010 (JP) .................................. 2010-221968

(51) Int. Cl.
G03B 42/06 (2006.01)
H04R 17/00 (2006.01)

(52) U.S. Cl.
USPC .......................................................... 367/140

(58) Field of Classification Search
USPC ...................................... 367/7, 140; 381/190
See application file for complete search history.

(56) References Cited

U.S. PATENT DOCUMENTS

| | | | | |
|---|---|---|---|---|
| 6,044,533 A | * | 4/2000 | Bureau et al. | 29/25.35 |
| 6,798,059 B1 | * | 9/2004 | Ishihara et al. | 257/700 |
| 8,077,549 B2 | * | 12/2011 | Jean et al. | 367/88 |
| 2006/0186765 A1 | * | 8/2006 | Hashimoto | 310/334 |
| 2007/0040469 A1 | * | 2/2007 | Yacoubian | 310/311 |
| 2011/0098550 A1 | * | 4/2011 | Yoda | 600/407 |
| 2013/0182530 A1 | * | 7/2013 | Ida | 367/7 |

FOREIGN PATENT DOCUMENTS

| | | |
|---|---|---|
| JP | H10-512680 A | 12/1998 |
| JP | 2000-138400 A | 5/2000 |
| JP | 2002-101496 A | 4/2002 |
| JP | 2002-142294 A | 5/2002 |
| JP | 2004-112326 A | 4/2004 |
| JP | 2006-25892 A | 2/2006 |
| JP | 2006-102135 A | 4/2006 |
| JP | 2008-28462 A | 2/2008 |
| JP | 2010-22812 A | 2/2010 |

OTHER PUBLICATIONS

International Preliminary Report on Patentability for international application No. PCT/JP2011/005167.
Office Action for Japanese Patent Application No. 2010-221968, issued by the Japanese Patent Office on Feb. 4, 2014.

* cited by examiner

Primary Examiner — Daniel Pihulic (57) ABSTRACT

Provided is a converter that converts sound waves into electrical signals, comprising a piezoelectric section including a plurality of piezoelectric elements that each convert a sound wave detected by a detection surface into one of the electrical signals; and a multilayer substrate to which the piezoelectric section is fixed. The multilayer substrate includes a plurality of signal wires that correspond respectively to the piezoelectric elements and each transmit the electrical signal output by the corresponding piezoelectric element; and a shield portion that electromagnetically shields at least a portion of the signal wires. The piezoelectric section is fixed to the multilayer substrate such that a surface of the multilayer substrate on which the piezoelectric elements are fixed is inclined with respect to the detection surfaces of the piezoelectric elements.

14 Claims, 8 Drawing Sheets

CONVERTER AND MEASURING APPARATUS

BACKGROUND

1. Technical Field

The present invention relates to a converter and a measurement apparatus.

2. Related Art

Conventional ultrasonic detection is known for generating an image showing the internal structure of a measurement target, such as a living organism, by irradiating the measurement target with ultrasonic waves and detecting the ultrasonic waves reflected from the measurement target. This type of ultrasonic detection uses a converter that converts the detected ultrasonic waves into electrical signals using a plurality of piezoelectric elements, as shown in Patent Documents 1 to 3, for example.

Patent Document 1: Japanese Patent Application Publication No. 2002-101496
Patent Document 2: Japanese Patent Application Publication No. 2004-112326
Patent Document 3: Japanese Patent Application Publication No. 2002-142294

A photoacoustic technique of irradiating a measurement target with light of a prescribed frequency is known as a method for measuring a measurement target with ultrasonic waves from the measurement target. With the photoacoustic technique, a periodic temperature change in the measurement target is created by the radiated light, and detecting the ultrasonic waves caused by fluctuation of the measurement target. With the photoacoustic technique, a converter is used to convert the detected ultrasonic waves into electrical signals.

However, with the photoacoustic technique, the intensity of the ultrasonic waves output from the measurement target is significantly lower than the intensity of the ultrasonic waves reflected by the measurement target during the ultrasonic wave detection. For example, the intensity of the ultrasonic waves detected using the photoacoustic technique are approximately 1% of the intensity of the ultrasonic waves detected using the ultrasonic wave detection. Therefore, the converter used for the photoacoustic technique must reduce external noise, electrical signal loss, and crosstalk between electrical signals, for example.

A conventional converter is known that transmits electrical signals from piezoelectric elements to cables through film wires. Furthermore, a conventional converter is known that transmits electrical signals from piezoelectric elements through via wires provided in a backing member of the piezoelectric elements. However, with film wires and via wires in the backing member, it is difficult to control the impedance and shield the transmission path, and therefore signal crosstalk and the like occurs in the film wire portion.

SUMMARY

Therefore, it is an object of an aspect of the innovations herein to provide a converter and a measurement apparatus, which are capable of overcoming the above drawbacks accompanying the related art. The above and other objects can be achieved by combinations described in the claims.

According to a first aspect of the present invention, provided is a converter that converts sound waves into electrical signals, comprising a piezoelectric section including a plurality of piezoelectric elements that each convert a sound wave detected by a detection surface into one of the electrical signals; and a multilayer substrate to which the piezoelectric section is fixed. The multilayer substrate includes a plurality of signal wires that correspond respectively to the piezoelectric elements and each transmit the electrical signal output by the corresponding piezoelectric element; and a shield portion that electromagnetically shields at least a portion of the signal wires. The piezoelectric section is fixed to the multilayer substrate such that a surface of the multilayer substrate on which the piezoelectric elements are fixed is inclined with respect to the detection surfaces of the piezoelectric elements.

According to a second aspect of the present invention, provided is a measurement apparatus that measures a measurement target, comprising a light source that irradiates the measurement target with light having an intensity modulated with a predetermined period; the converter of the first aspect that converts the sound waves output from the measurement target in response to the radiated light into the electrical signals; and an image generating section that generates an image corresponding to the electrical signals resulting from the conversion by the converter.

The summary clause does not necessarily describe all necessary features of the embodiments of the present invention. The present invention may also be a sub-combination of the features described above.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
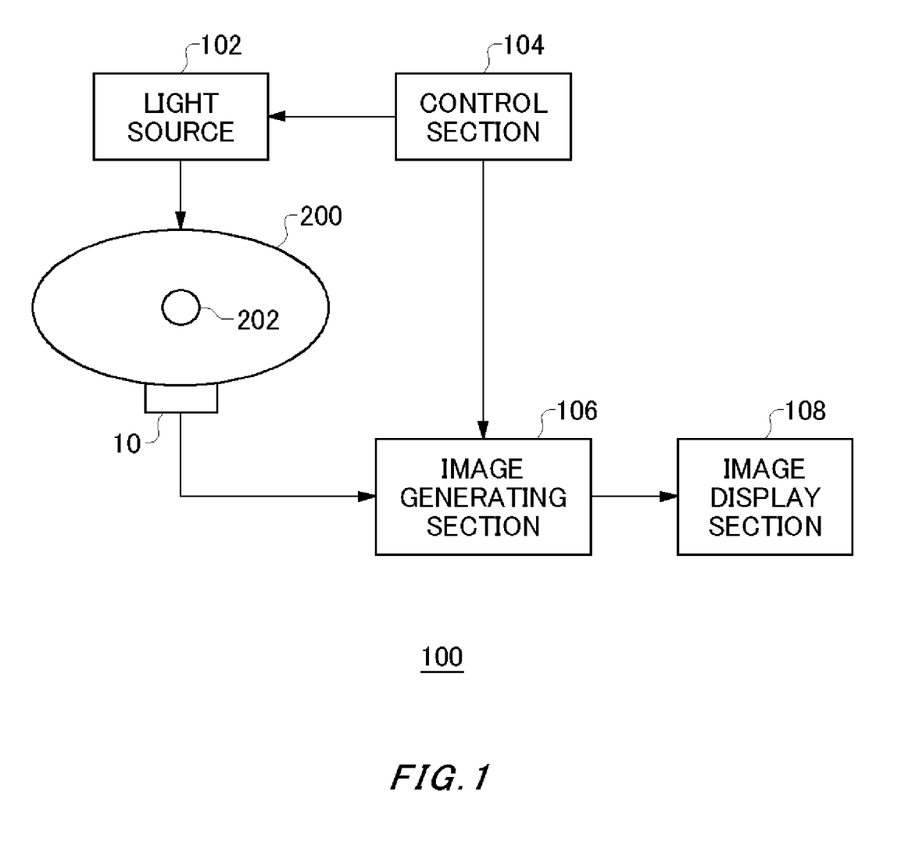
FIG. 1 shows an exemplary configuration of a measurement apparatus 100 for measuring a measurement target 200.

FIG. 1 shows an exemplary configuration of a measurement apparatus 100 for measuring a measurement target 200. The measurement target 200 may be a biological material, for example. The measurement apparatus 100 measured the internal structure or the like of the measurement target 200, using a photoacoustic technique. The measurement apparatus 100 measures the internal structure or the like of the measurement target 200 by detecting sound waves, such as ultrasonic waves, output from the measurement target 200 when the measurement target 200 is irradiated with light.

More specifically, the measurement apparatus 100 irradiates the measurement target 200 with light of a prescribed frequency. At this time, an object to be measured 202 selectively absorbs the light and periodically exhibit adiabatic expansion, thereby generating ultrasonic waves. The ultrasonic waves have a period corresponding to the radiated light. The phase, amplitude, and the like of the sound waves generated by the object to be measured 202 correspond to physical properties such as the thermal expansion coefficient and depth of the object to be measured 202 in the measurement target 200. Therefore, by irradiating a plurality of positions with light and detecting the sound waves at each irradiated position, the physical properties and positions of objects to be measured within the measurement target 200 can be measured.

The measurement apparatus 100 includes a converter 10, a light source 102, an image generating section 106, a control section 104, and an image display section 108. The light source 102 irradiates the measurement target 200 with pulse light that includes pulses with a predetermined period.

The converter 10 detects the sound waves output from the measurement target 200 in response to the light radiated from the light source 102. The converter 10 may include a plurality of piezoelectric elements. Each piezoelectric element converts sound waves output from a different position on the surface of the measurement target 200 into an electrical signal, and outputs the electrical signal to the image generating section 106.

The image generating section 106 generates an image showing the internal structure of the measurement target 200, using the electrical signals input from the converter 10. The image generating section 106 may generate an image showing a distribution of physical property values within the measurement target 200, based on the phase, amplitude, and the like of the electrical signals corresponding respectively to the different positions of the measurement target 200.

The control section 104 controls the intensity, period, and phase of the light radiated from the light source 102. The control section 104 may notify the image generating section 106 concerning the intensity, period, and phase of the light radiated from the light source 102. The image generating section 106 may generate the image based on information received in the notification from the control section 104 and the electrical signals input from the converter 10. The image display section 108 displays the image generated by the image generating section 106.

Figure 2:
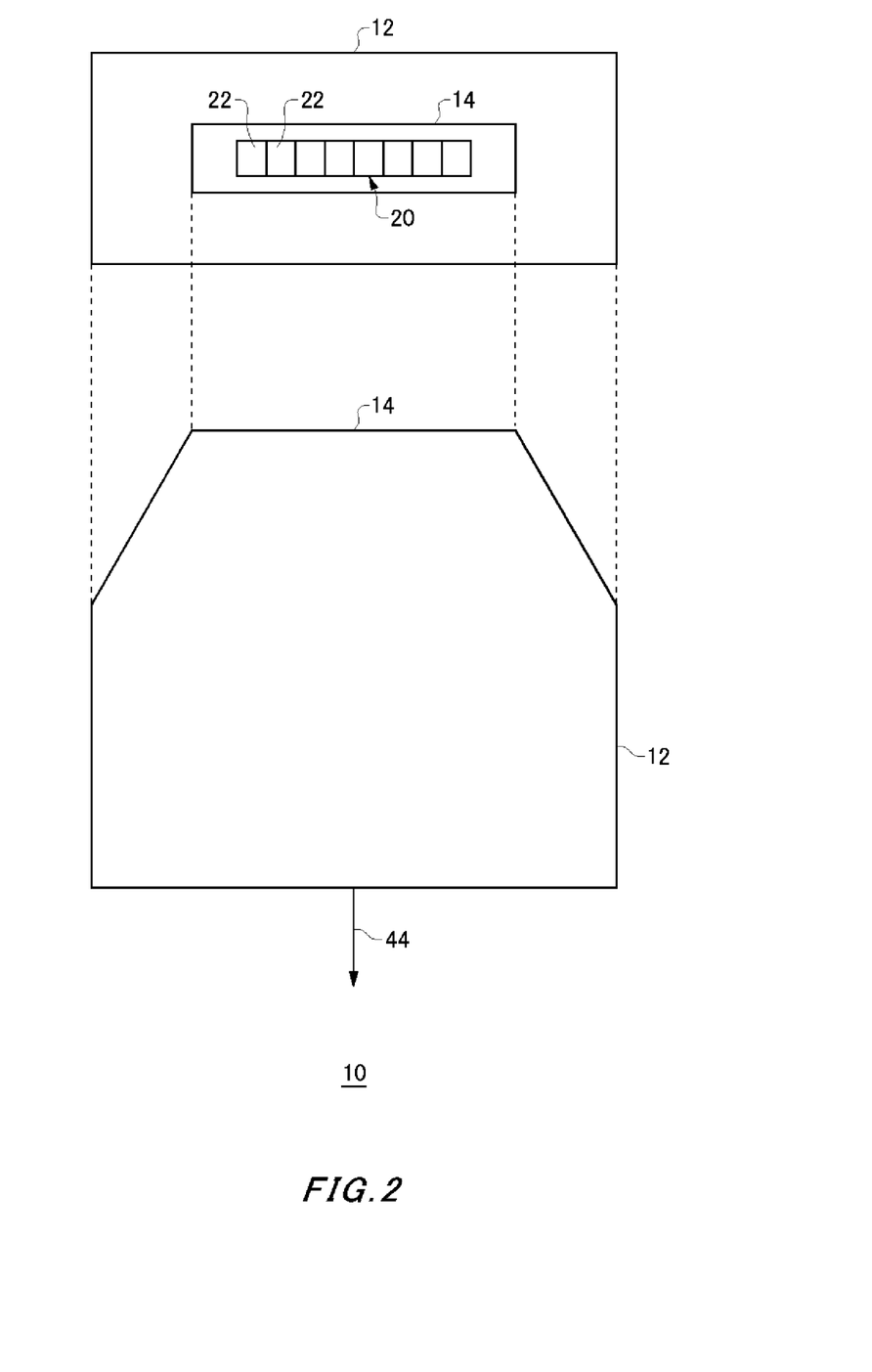
FIG. 2 shows an exemplary external appearance of the converter 10.

FIG. 2 shows an exemplary external appearance of the converter 10. The top portion of FIG. 2 is a front view of the converter 10, and the lower portion of FIG. 2 is a top view of the converter 10. The converter 10 includes a front surface section 14 that is arranged to face the measurement target 200. A sound wave detection surface of the piezoelectric section 20 is exposed in the front surface section 14. The piezoelectric section 20 includes a plurality of piezoelectric elements 22.

The converter 10 includes a gripping section 12. The gripping section 12 may be gripped by a user. The width of the front surface section 14 may be approximately the same as the overall width of the plurality of piezoelectric sections 20. The width of the gripping section 12 may be greater than the width of the front surface section 14. Since the overall width of the plurality of piezoelectric sections 20 is small, forming the gripping section 12 with a larger width enables easy gripping for the user.

The converter 10 transmits the electrical signals output by the piezoelectric section 20 to the image generating section 106, via a cable 44. Within the converter 10, a multilayer substrate is provided for transmitting the electrical signals output by the piezoelectric section 20 to the cable 44.

Figure 3A:
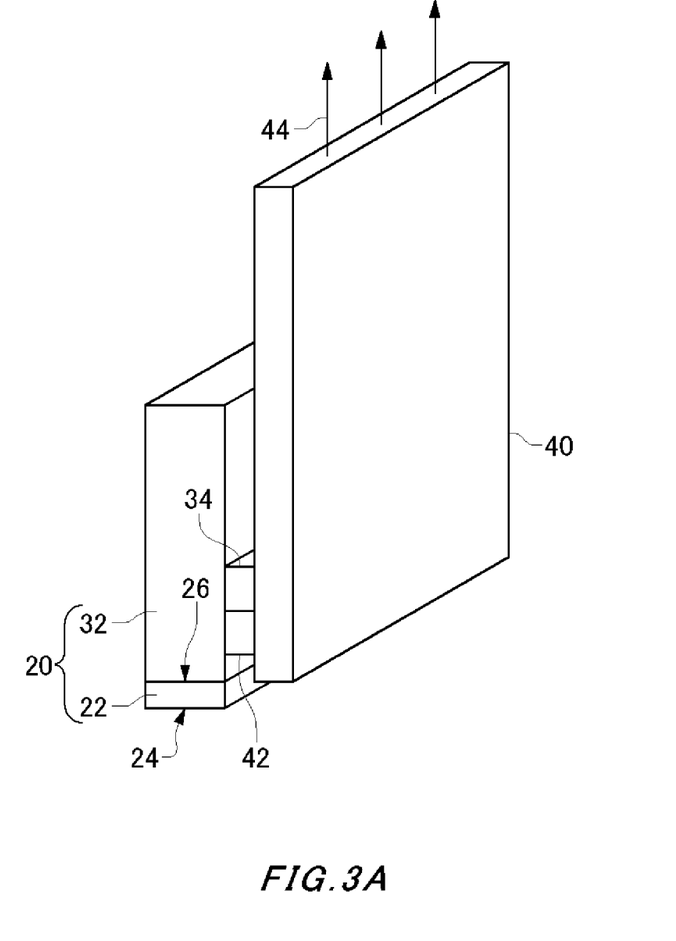
FIG. 3A shows a state in which the piezoelectric section 20 is fixed to the multilayer substrate 40.
Figure 3B:
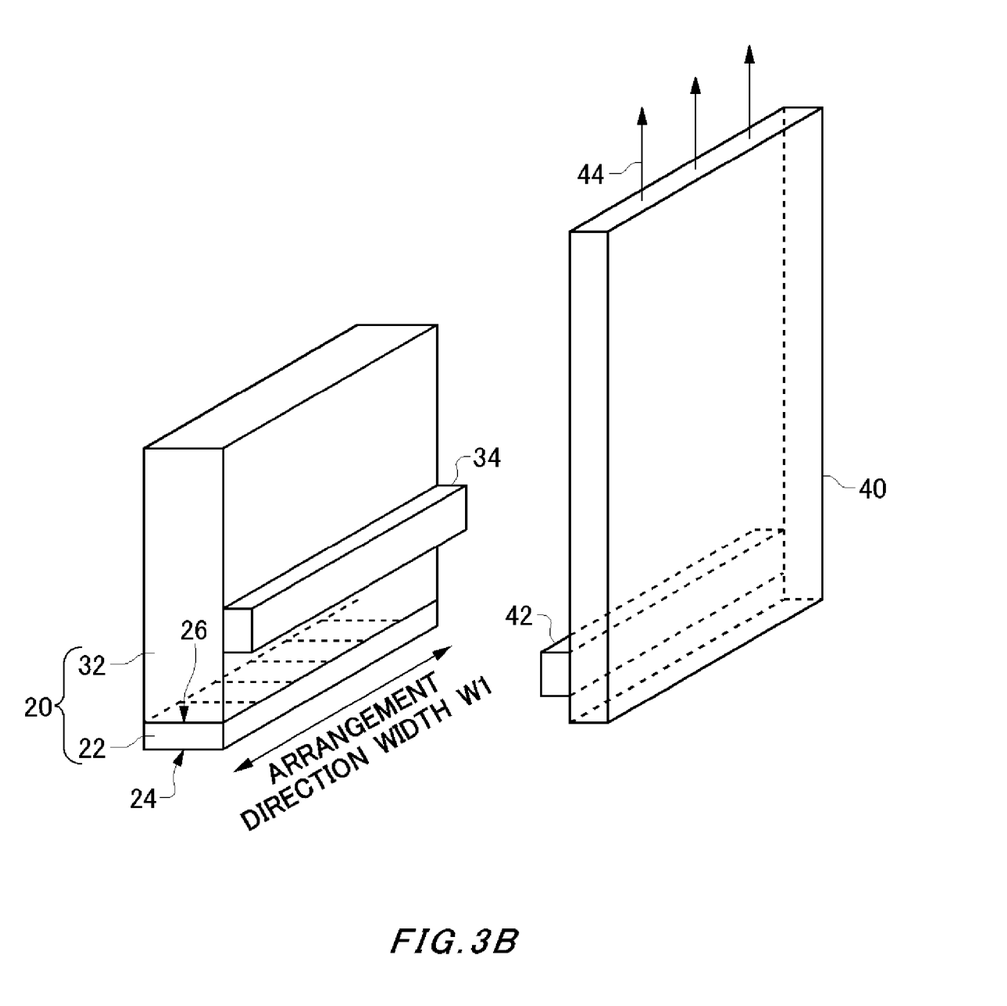
FIG. 3B shows a state in which the piezoelectric section 20 is distanced from the multilayer substrate 40.

FIGS. 3A and 3B show exemplary configurations of the piezoelectric section 20 and the multilayer substrate 40 provided within the converter 10. FIG. 3A shows a state in which the piezoelectric section 20 is fixed to the multilayer substrate 40. FIG. 3B shows a state in which the piezoelectric section 20 is distanced from the multilayer substrate 40.

The piezoelectric section 20 includes the plurality of piezoelectric elements 22, a back surface section 32, and a piezoelectric-side connecting section 34. Each piezoelectric element 22 converts the sound waves detected by the respective detection surface 24 into an electrical signal. The piezoelectric elements 22 are arranged adjacent to each other in a straight line, in a prescribed arrangement direction. Here, "adjacent" also includes a case in which a wall or the like for vibration isolation is provided between two piezoelectric elements 22. Furthermore, the piezoelectric elements 22 preferably have detection surfaces 24 with the same height, such that the detection surfaces 24 all fall within the same plane. The pitch at which the piezoelectric elements 22 are arranged is 1 mm or less, for example.

The back surface section 32 is provided on the back surface 26 side of the detection surfaces 24 of the piezoelectric elements 22, and absorbs the sound waves emitted from the back surfaces 26 of the piezoelectric elements 22. The back surface section 32 may be provided in common to the plurality of piezoelectric elements 22, or a single back surface section 32 may be provided independently for each piezoelectric element 22.

The piezoelectric-side connecting section 34 is provided on a surface of the piezoelectric section 20 facing the multilayer substrate 40. The piezoelectric-side connecting section 34 in this example is provided on the surface of the back surface section 32 facing the multilayer substrate 40. The piezoelectric-side connecting section 34 is electrically connected to the piezoelectric elements 22, and receives the electrical signals output respectively by the piezoelectric elements 22.

The piezoelectric-side connecting section 34 is preferably provided near the piezoelectric elements 22. The piezoelectric-side connecting section 34 may be provided closer to the piezoelectric elements 22 than the center of the back surface section 32. Furthermore, the piezoelectric-side connecting section 34 may be provided in contact with an electrode portion of a vibration portion of the piezoelectric elements 22.

Wires that connect the piezoelectric-side connecting section 34 to the electrode portion of the piezoelectric elements 22 may be formed along the outer surface of the back surface section 32, or may be formed within the back surface section 32. The length of the wiring connecting the piezoelectric-side connecting section 34 to the piezoelectric elements 22 is less than the thickness of the back surface section 32 in a direction perpendicular to the back surface 26. With this configuration, the transmission path from the piezoelectric elements 22 to the piezoelectric-side connecting section 34 can be shortened.

The multilayer substrate 40 includes a substrate-side connecting section 42 that connects the multilayer substrate 40 to the piezoelectric-side connecting section 34, on the surface facing the piezoelectric section 20. The multilayer substrate 40 receives the electrical signals output by the piezoelectric elements 22 via the substrate-side connecting section 42, and transmits the electrical signals to the cable 44.

The piezoelectric section 20 is fixed to the multilayer substrate 40 such that the surface of the multilayer substrate 40 on which the piezoelectric elements 22 are fixed and the detection surfaces 24 of the piezoelectric elements 22 are inclined relative to each other. In other words, the detection surfaces 24 and the fixing surface of the multilayer substrate 40 are not parallel. The piezoelectric section 20 may be fixed such that the detection surfaces 24 and the fixing surface of the multilayer substrate 40 are substantially perpendicular to each other.

The piezoelectric-side connecting section 34 and the substrate-side connecting section 42 may be electrode pads. In this case, the piezoelectric-side connecting section 34 and the substrate-side connecting section 42 may be soldered. The piezoelectric-side connecting section 34 and the substrate-side connecting section 42 may be connectors. In this case, the piezoelectric section 20 is fixed to the surface of the multilayer substrate 40 that is substantially perpendicular to the detection surface 24 of the piezoelectric elements 22, by interlocking the piezoelectric-side connecting section 34 with the substrate-side connecting section 42. As a result, the multilayer substrate 40 can be arranged near the piezoelectric elements 22.

It is possible to fix the piezoelectric elements 22 to a surface of the multilayer substrate that is parallel to the detection surface 24 of the piezoelectric elements 22, but in this case, the vibration in a direction perpendicular to the detection surface 24 of the piezoelectric elements 22 is easily transmitted to the multilayer substrate, which results in the propagation of vibration between the piezoelectric elements 22. Furthermore, when connecting the electrodes of the piezoelectric elements 22 to the wires on this multilayer substrate, the back surface section 32 must be omitted or wiring penetrating through the back surface section 32 must be provided. In contrast to this, with the converter 10 of the present example, the detection surface 24 of the piezoelectric elements 22 is arranged to be inclined relative to the multilayer substrate 40, and therefore it is difficult for the vibration of the detection surface 24 to be transmitted to the multilayer substrate 40. Furthermore, the back surface section 32 can be provided to absorb sound waves from the back surface 26.

Figure 4:
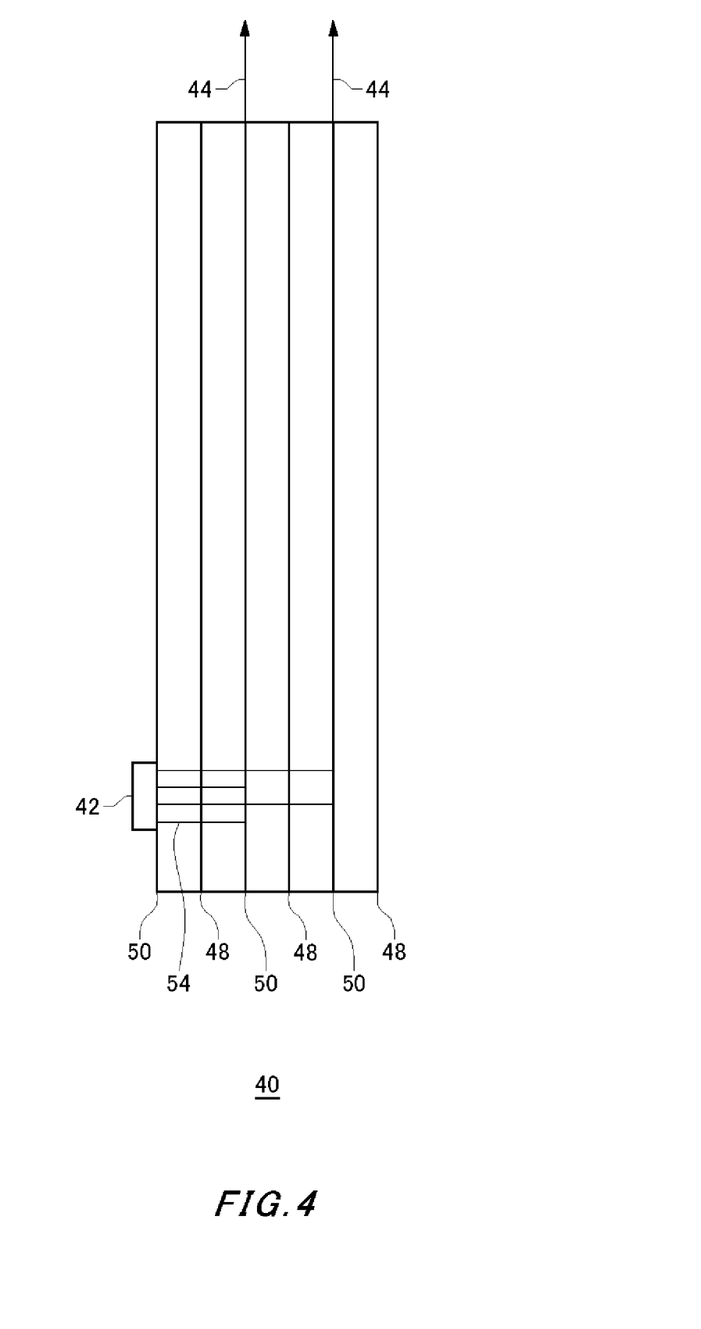
FIG. 4 shows an exemplary cross section of the multilayer substrate 40.

FIG. 4 shows an exemplary cross section of the multilayer substrate 40. The multilayer substrate 40 may include wiring layers 50 in which signal wires are formed and ground layer 48 in which ground patterns are formed, layered in an alternating manner. Each terminal of the substrate-side connecting section 42 is connected to a signal wire formed in one of the wiring layers 50, through a via wire 54. The signal wires correspond to the piezoelectric elements 22, and each signal wire transmits the electrical signal output by the corresponding piezoelectric element 22 to the cable 44.

Signal wires corresponding to adjacent piezoelectric elements 22 may be provided in different layers of the multilayer substrate 40. In other words, via wires 54 corresponding to adjacent piezoelectric elements 22 may be connected to different layers of the multilayer substrate 40.

The ground patterns provided in the ground layers 48 function as shield portions that electromagnetically shield at least a portion of the signal wires. The ground patterns may be formed over the entire surface of each ground layer 48, and may each have the same pattern as the signal wires formed in the adjacent interconnection layer 50. The ground pattern is formed of a conductive material. A ground potential is provided to each of the ground patterns.

With this configuration, the signal wires in the multilayer substrate 40 can be shielded. Furthermore, since the piezoelectric elements 22 can be arranged near the multilayer substrate 40, the transmission paths that are not shielded are short. As a result, loss, crosstalk, external noise, and the like in the electrical signals output by the piezoelectric elements 22 can be decreased. A plurality of via wires 54 may be formed in a single interconnection layer 50. In other words, a plurality of signal wires may be formed in a single interconnection layer 50.

Figure 5:
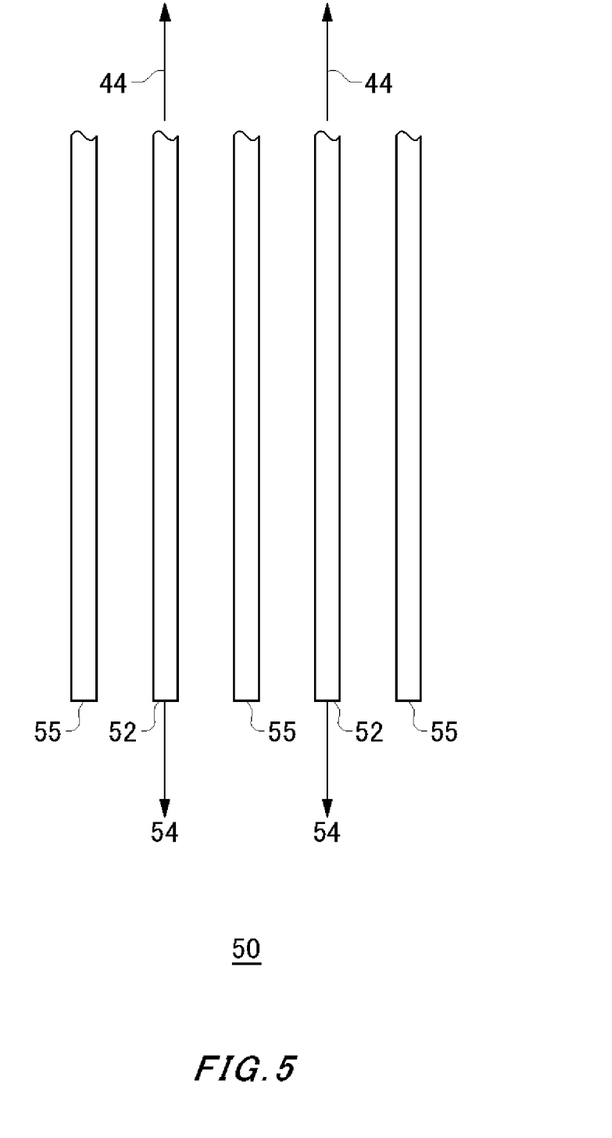
FIG. 5 shows an exemplary interconnection layer 50.

FIG. 5 shows an exemplary interconnection layer 50. A plurality of signal wires 52 are formed in the interconnection layer 50 of this example. Each signal wire 52 is connected to an electrode portion of the corresponding piezoelectric element 22, through a via wire 54, the substrate-side connecting section 42, and the piezoelectric-side connecting section 34. Each signal wire 52 transmits the electrical signal output by the corresponding piezoelectric element 22 to the cable 44.

In the interconnection layer 50, ground wires 55 are formed parallel to the signal wires 52. The ground wires 55 may be formed on both sides of each signal wire 52. The ground wires 55 function as shield portions that electromagnetically shield at least a portion of the signal wires 52. The ground wires 55 may be provided with a ground potential.

Figure 6:
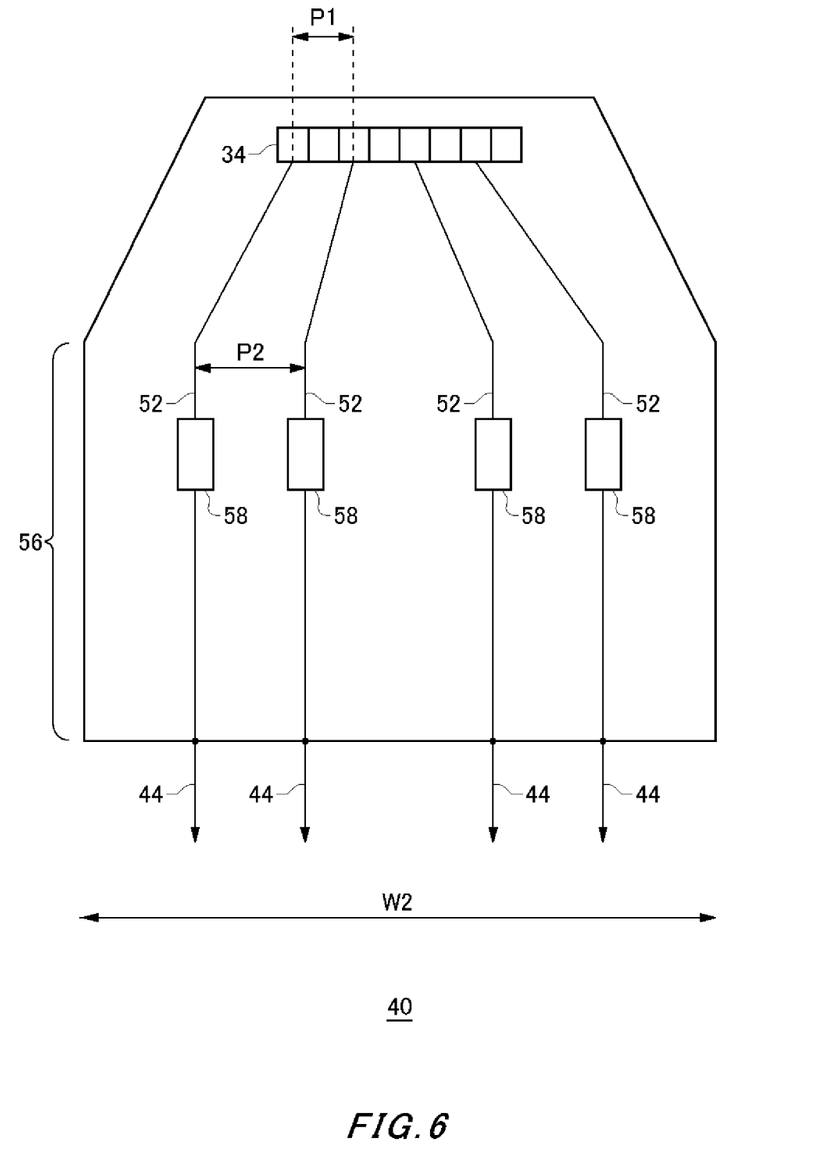
FIG. 6 shows an exemplary configuration of the multilayer substrate 40.

FIG. 6 shows an exemplary configuration of the multilayer substrate 40. The multilayer substrate 40 of this example includes a region 56 in which the width W2 in the arrangement direction of the piezoelectric elements 22 is greater than the overall width W1 (see FIG. 3B) of the piezoelectric elements 22 arranged adjacent thereto. As shown in FIG. 2, the converter 10 includes the gripping section 12 having a large width, and therefore the region 56 of the multilayer substrate 40 having a large width can be provided within the gripping section 12.

In the region 56, the pitch P2 with which the signal wires 52 are provided in the arrangement direction is greater than the pitch P1 of the corresponding terminals in the piezoelectric-side connecting section 34. In other words, the pitch P2 of the signal wires 52 near the cables 44 is greater than the pitch P1 of the signal wires 52 near the piezoelectric-side connecting section 34. With this configuration, crosstalk between the signal wires 52 can be decreased.

In the region 56, a ground wire 55 may also be provided between each pair of adjacent signal wires 52. The multilayer substrate 40 may have a square shape. In other words, the multilayer substrate 40 may have a width W2, which is the same as that of the region 56, near the piezoelectric-side connecting section 34. In this case, the front surface section 14 of the converter 10 may have the same width as the gripping section 12.

Furthermore, signal processors 58 may be provided in the multilayer substrate 40. A signal processor 58 may be provided for each signal wire 52. Each signal processor 58 may function as a signal converting section that converts the electrical signal transmitted on the corresponding signal wire 52 into a different signal and transmits this converted signal. Each signal processor 58 may convert the electrical signal into a digital signal or a differential signal.

With this configuration, the electrical signals output by the piezoelectric elements 22 can be converted into digital signals or differential signals near the piezoelectric elements 22. In other words, the region in which the electrical signals, which are easily affected by noise, are transmitted can be set to be the short region from the piezoelectric elements 22 to the signal processors 58. By converting the electrical signals into digital signals or differential signals the signal components can be accurately extracted on the reception side even when there is noise occurring downstream from the signal processors 58.

Furthermore, each signal processor 58 may function as an amplitude amplifying section that amplifies the amplitude of the electrical signal transmitted by the corresponding signal wire 52 and transmits the amplified signal. In this way, the ratio of the signal components of the electrical signals to the noise occurring in the transmission path downstream of the signal processors 58 is high, and so the signals can be accurately transmitted. Furthermore, since the signal processors 58 are provided near the piezoelectric elements 22, the transmission region that is easily affected by noise can be shortened.

In this way, by providing the multilayer substrate 40 with the signal processors 58, the signal transmission accuracy in the cables 44 can be improved. Furthermore, each signal processor 58 may be provided in the region 56. In the region 56, the pitch between the signal wires 52 is large, and therefore the signal processors 58 can be easily provided in the region 56. In particular, the amplitude of the sound waves detected in the photoacoustic technique are low and the signals are easily affected by noise, attenuation, or the like in the signal transmission path from the piezoelectric elements 22 to the image generating section 106, but by using the converter 10 of this example, the accuracy and efficiency of the signal transmission can be improved.

FIG. 6 describes an example in which the converter 10 includes a plurality of piezoelectric elements 22, but the converter 10 may have the same configuration even if there is only one piezoelectric element 22. In this case, the signal transmission can be improved by providing the signal processor 58 in the multilayer substrate 40. Furthermore, the function of the signal processor 58 is not limited to the function described above. For example, the signal processor 58 may function as a filter that passes a prescribed frequency component.

Figure 7:
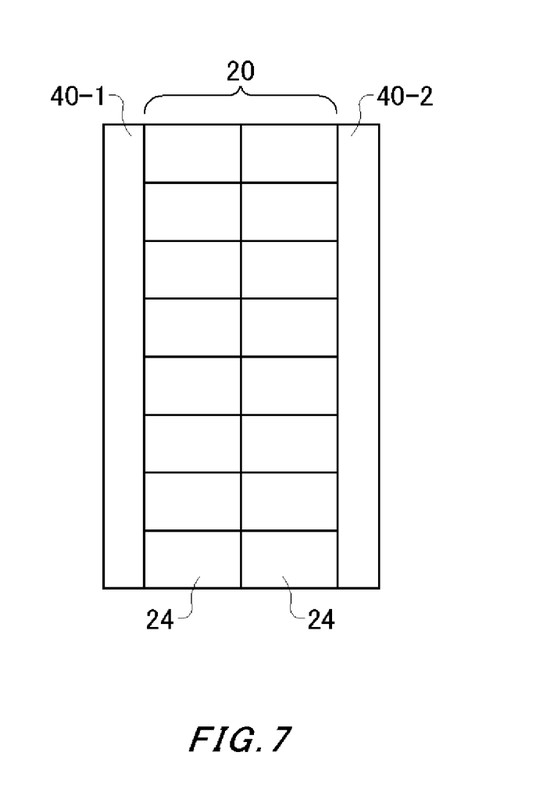
FIG. 7 shows another exemplary configuration of the piezoelectric section 20.

FIG. 7 shows another exemplary configuration of the piezoelectric section 20. In the piezoelectric section 20 of this example, the plurality of piezoelectric elements 22 are provided such that the detection surfaces 24 form a two-dimensional matrix configuration. This two-dimensional matrix configuration refers to a configuration in which the piezoelectric elements 22 are arranged periodically along at least two arrangement axes. The piezoelectric elements 22 in this example are arranged along two arrangement axes that are orthogonal to each other.

Multilayer substrates 40 are provided at least at two sides of the two-dimensional matrix configuration. In this example, a first multilayer substrate 40-1 and a second multilayer substrate 40-2 are provided at opposite sides of the two-dimensional matrix configuration. Each piezoelectric element 22 may be electrically connected to whichever of the multilayer substrates 40 is closest. With this configuration, the distance over which the electrical signals are transmitted between the multilayer substrates 40 and the piezoelectric elements 22 provided in the two-dimensional matrix configuration can be shortened.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

What is claimed is:

1. A converter that converts sound waves into electrical signals, comprising:
   a piezoelectric section including a plurality of piezoelectric elements that each convert a sound wave detected by a detection surface into one of the electrical signals; and
   a multilayer substrate to which the piezoelectric section is fixed, wherein
   the multilayer substrate includes:
      a plurality of signal wires that correspond respectively to the piezoelectric elements and each transmit the electrical signal output by the corresponding piezoelectric element; and
      a shield portion that electromagnetically shields at least a portion of the signal wires, and
   the piezoelectric section is fixed to the multilayer substrate such that a surface of the multilayer substrate on which the piezoelectric elements are fixed is inclined with respect to the detection surfaces of the piezoelectric elements.

2. The converter according to claim 1, wherein
   the piezoelectric section includes, on a surface thereof facing the multilayer substrate, a piezoelectric-side connecting section that is electrically connected to each of the piezoelectric elements, and
   the multilayer substrate includes, on a surface thereof facing the piezoelectric section, a substrate-side connecting section that is electrically connected to each of the signal wires and also connects to the piezoelectric-side connecting section.

3. The converter according to claim 2, wherein
   the piezoelectric section includes a back surface section that is provided on back surfaces of the detection surfaces of the piezoelectric elements, and that absorbs sound waves emitted from the back surfaces of the piezoelectric elements, and
   the piezoelectric-side connecting section is provided on a surface of the back surface section facing the multilayer substrate.

4. The converter according to claim 3, wherein
   the piezoelectric-side connecting section is provided to the piezoelectric element side of the center of the back surface section.

5. The converter according to claim 1, further comprising:
   in the multilayer substrate, a signal converting section that is provided to correspond to at least one of the plurality of signal wires, and that converts the electrical signal transmitted on the corresponding signal wire into a different signal and transmits the converted signal.

6. The converter according to claim 1, further comprising:
   in the multilayer substrate, an amplitude amplifying section that is provided to correspond to at least one of the plurality of signal wires, and that amplifies the amplitude of the electrical signal transmitted by the corresponding signal wire and transmits the amplified signal.

7. The converter according to claim 1, wherein
   at least a portion of the piezoelectric elements are arranged sequentially and adjacently in a straight line, and signal wires corresponding to adjacent piezoelectric elements are provided in different layers of the multilayer substrate.

8. The converter according to claim 2, wherein
   at least a portion of the piezoelectric elements are arranged sequentially and adjacently in a straight line,
   the multilayer substrate includes a region in which width of the multilayer substrate in an arrangement direction, which is a direction in which the piezoelectric elements are arranged adjacently, is greater than total width of the piezoelectric elements arranged adjacently, and in the region, pitch with which the signal wires are provided in the arrangement direction is greater than pitch of the terminals corresponding to the piezoelectric-side connecting section.

9. The converter according to claim 1, wherein
the piezoelectric elements are arranged in a two-dimensional matrix configuration, and
a plurality of the multilayer substrates are provided at least at two sides of the matrix configuration.

10. The converter according to claim 1, wherein
the piezoelectric section is fixed to a surface of the multilayer substrate that is substantially perpendicular to the detection surfaces of the piezoelectric elements.

11. A measurement apparatus that measures a measurement target, comprising:
a light source that irradiates the measurement target with light having an intensity modulated with a predetermined period;
the converter according to claim 1 that converts the sound waves output from the measurement target in response to the radiated light into the electrical signals; and
an image generating section that generates an image corresponding to the electrical signals resulting from the conversion by the converter.

12. The converter according to claim 5, wherein
the different signal is a digital signal.

13. The converter according to claim 5, wherein
the different signal is a differential signal.

14. The converter according to claim 3, wherein
the length of wiring connecting the piezoelectric-side connecting section to the piezoelectric elements is less than the thickness of the back surface section in a direction perpendicular to the back surfaces.

* * * * *